(12) United States Patent
Callister

(10) Patent No.: US 6,752,786 B2
(45) Date of Patent: Jun. 22, 2004

(54) MOVING HEAT EXCHANGE CATHETER SYSTEM

(75) Inventor: Jeff Callister, Redwood City, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

(21) Appl. No.: 09/872,818

(22) Filed: May 31, 2001

(65) Prior Publication Data

US 2002/0183691 A1 Dec. 5, 2002

(51) Int. Cl.$^7$ .................................................. A61E 7/12
(52) U.S. Cl. .......................... 604/113; 604/22; 604/105
(58) Field of Search .................. 604/113, 114, 604/22; 606/20, 21, 27; 607/105

(56) References Cited

U.S. PATENT DOCUMENTS

| | | | | |
|---|---|---|---|---|
| 4,941,475 A | * | 7/1990 | Williams et al. | 128/692 |
| 5,176,141 A | * | 1/1993 | Bom et al. | 128/662.06 |
| 5,269,758 A | | 12/1993 | Taheri | |
| 5,304,214 A | * | 4/1994 | DeFord et al. | 607/105 |
| 5,540,656 A | * | 7/1996 | Pflueger et al. | 604/22 |
| 5,837,003 A | | 11/1998 | Ginsburg | |
| 6,096,068 A | | 8/2000 | Dobak, III et al. | |
| 6,126,684 A | * | 10/2000 | Gobin et al. | 607/113 |
| 6,241,722 B1 | * | 6/2001 | Dobak et al. | 606/23 |
| 6,283,989 B1 | * | 9/2001 | Laufer et al. | 607/96 |
| 6,299,599 B1 | * | 10/2001 | Pham et al. | 604/113.6 |
| 6,358,273 B1 | * | 3/2002 | Strul et al. | 607/96 |
| 6,440,158 B1 | * | 8/2002 | Saab | 607/105 |
| 6,486,208 B1 | | 11/2002 | Castillo et al. | |
| 2002/0077665 A1 | * | 6/2002 | Kordis et al. | 607/1 |
| 2002/0120314 A1 | * | 8/2002 | Evans et al. | 607/96 |
| 2002/0151880 A1 | * | 10/2002 | Lafontaine | 606/21 |

FOREIGN PATENT DOCUMENTS

| WO | WO 99/66970 | 12/1999 | |
|---|---|---|---|
| WO | WO 00/09054 | 2/2000 | ............. A61F/7/12 |
| WO | WO 00/62837 | 10/2000 | |

\* cited by examiner

Primary Examiner—Henry Bennett
Assistant Examiner—Camtu Nguyen
(74) Attorney, Agent, or Firm—Robert D. Buyan; Stout, Uxa, Buyan & Mullins, LLP

(57) ABSTRACT

A catheter system for controlling the body temperature of a patient by modifying the temperature of blood flowing within a blood vessel of the patient. The catheter system comprises a catheter body having a heat exchange region in contact with the blood; and a mechanism for moving the heat exchange surface, thereby increasing heat exchange between the heat exchange surface and blood flowing past the heat exchange surface. Various methods of moving the heat exchange surface are disclosed.

13 Claims, 8 Drawing Sheets

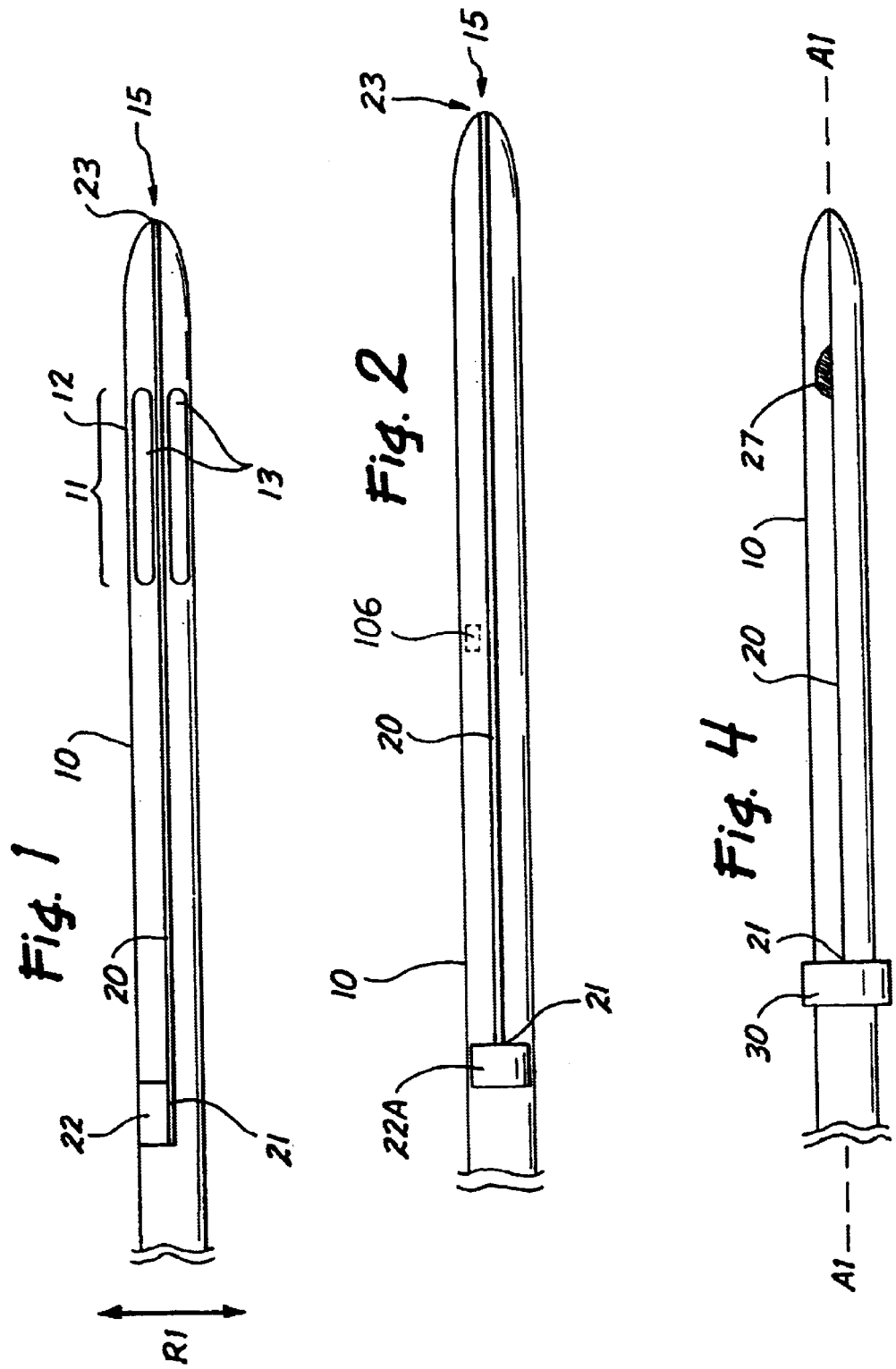

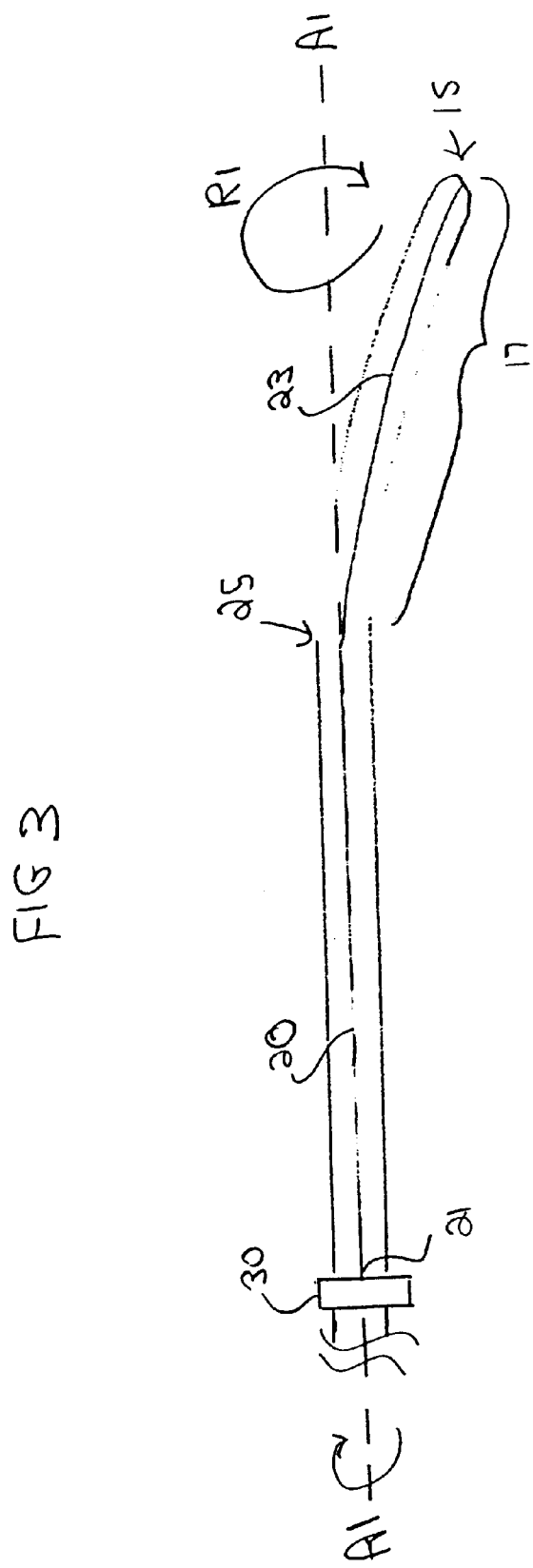

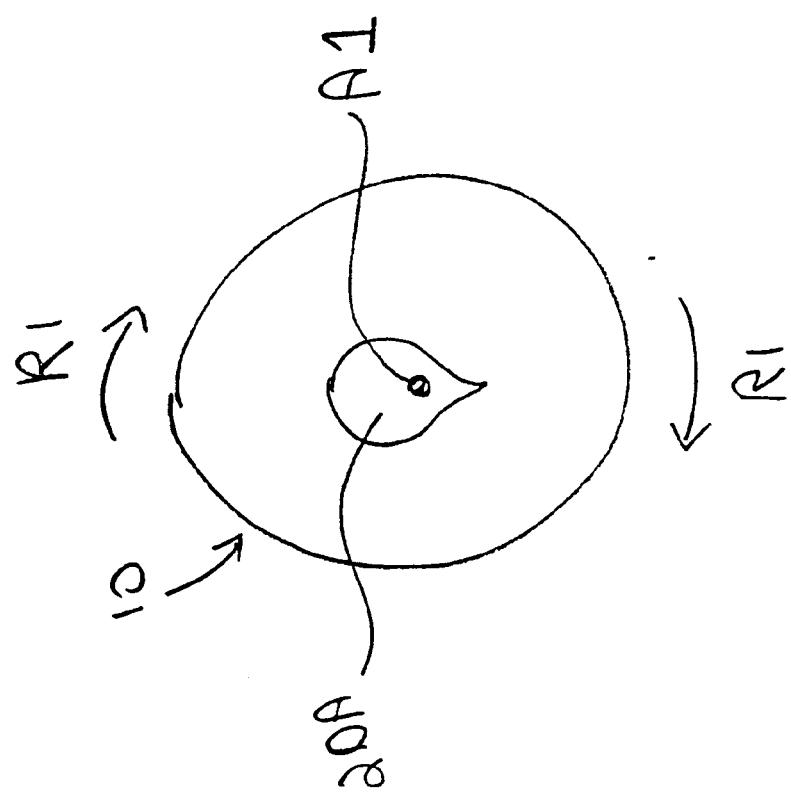

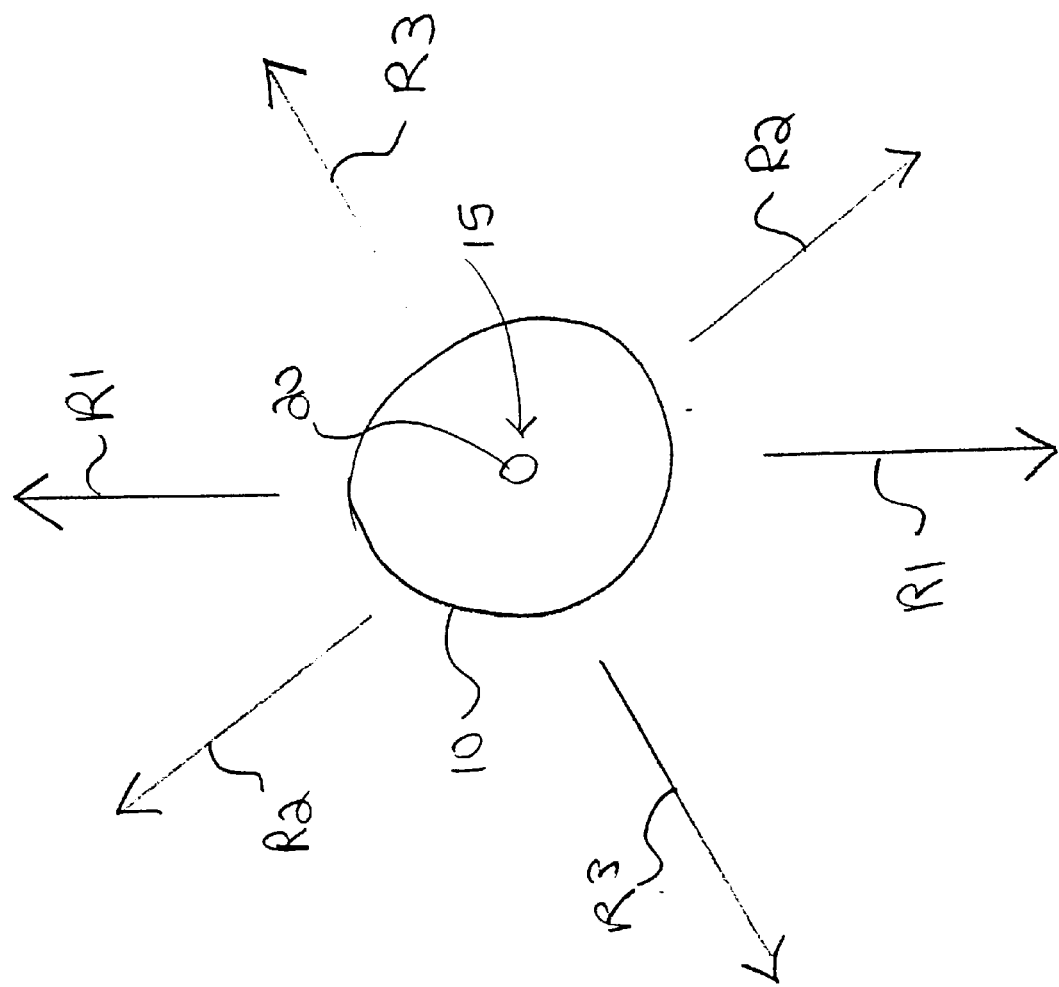

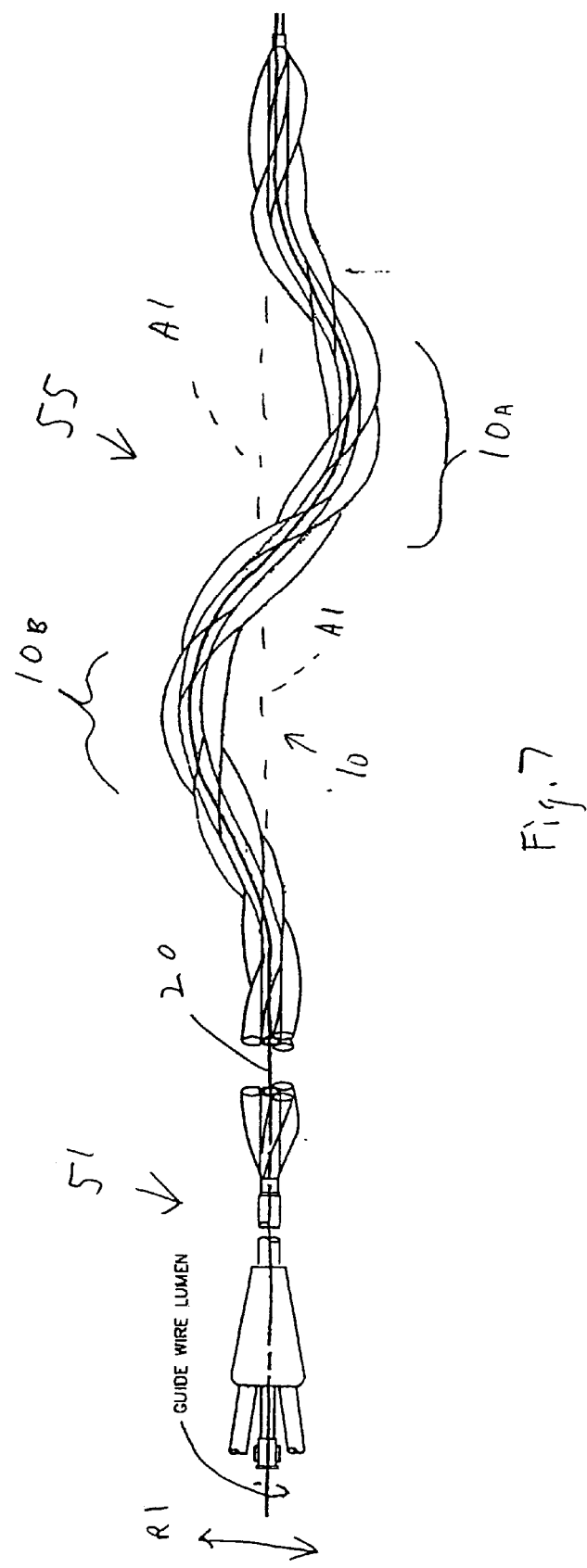

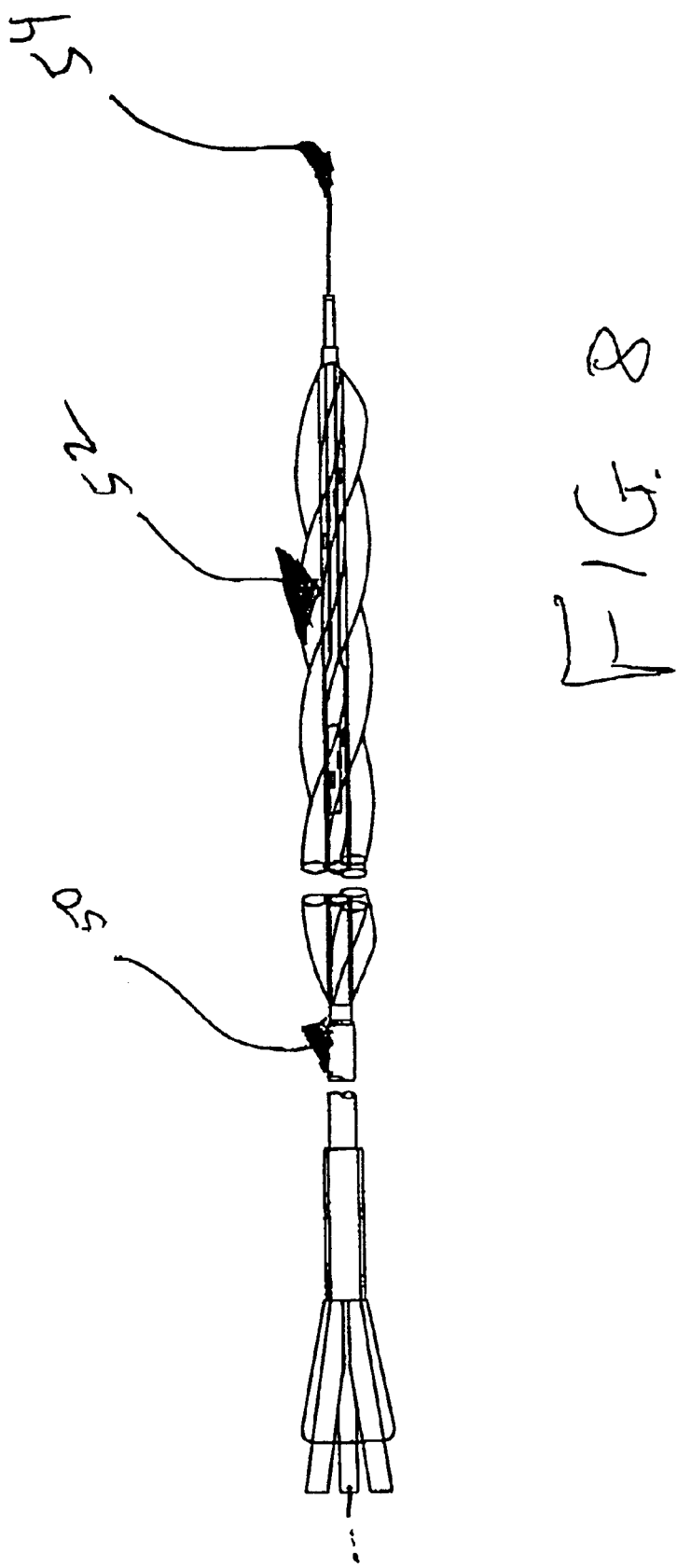

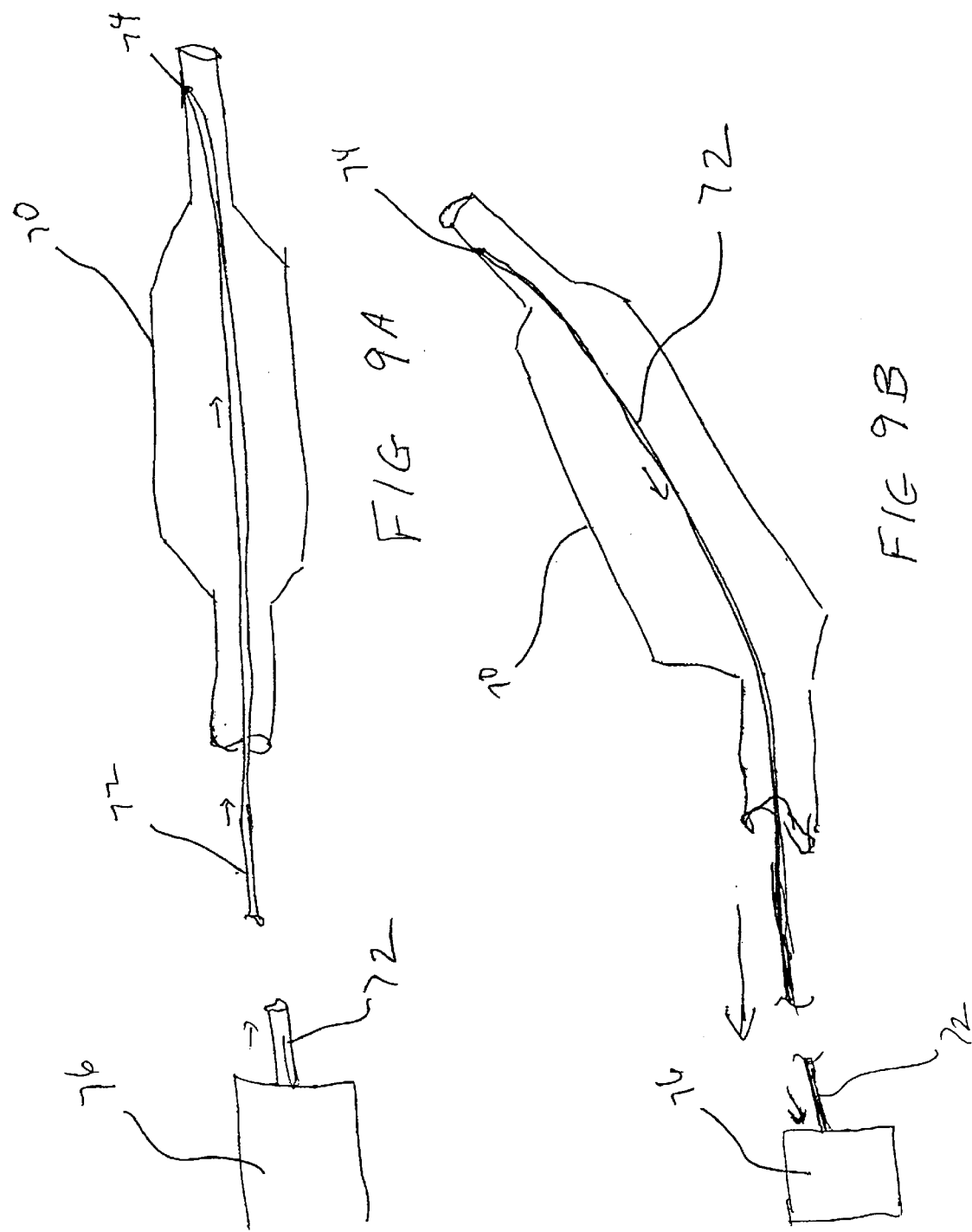

MOVING HEAT EXCHANGE CATHETER SYSTEM

TECHNICAL FIELD

In general, the present invention relates to heat exchange catheters adapted to control or modify a patient's internal body temperature, and in particular, intravascular heat exchange catheter systems with heat exchange surfaces having a source of motion for generating sufficient motion to increase heat transfer between the heat exchange surface and the blood flowing past the heat exchange surface.

BACKGROUND OF THE INVENTION

Under ordinary circumstances, the thermoregulatory system of the human body maintains a near constant temperature of about 37° C. (98.6° F.), a temperature referred to as normothermia.

For various reasons, however, a person may develop a body temperature that is below normothermia, a condition known as hypothermia, or a temperature that is above normothermia, a condition known as hyperthermia. Hypothermia and hyperthermia are generally harmful, and if severe, the patient is generally treated to reverse the condition and return the patient to normothermia. Accidental hypothermia significant enough to require treatment may occur in patients exposed to overwhelming cold stress in the environment or whose thermoregulatory ability has been lessened due to injury, illness or anesthesia. For example, this type of hypothermia sometimes occurs in patients suffering from trauma or as a complication in patients undergoing surgery. Likewise, examples of hyperthermia include exposure to overwhelming exposure to hot environmental stimulation, injury or illness, or complications of anesthesia.

However, in certain other situations hyperthermia and especially hypothermia may be desirable and may even be intentionally induced. For instance, hypothermia is generally recognized as being neuroprotective, and may, therefore, be induced in conjunction with treatments for ischemic or hemorrhagic stroke, blood deprivation such as caused by cardiac arrest, intracerebral or intracranial hemorrhage, and head and spinal trauma. In each of these instances, damage to neural tissue may occur because of ischemia, increased intracranial pressure, edema or other processes, often resulting in a loss of cerebral function and permanent neurological deficits.

Other examples where hypothermia may be neuroprotective include periods of cardiac arrest in myocardial infarction and heart surgery, neurosurgical procedures such as aneurysm repair surgeries, endovascular aneurysm repair procedures, spinal surgeries, procedures where the patient is at risk for brain, cardiac or spinal ischemia such as beating heart by-pass surgery or any surgery where the blood supply to the heart, brain or spinal cord may be temporarily interrupted.

Hypothermia has also been found to be advantageous as a treatment to protect both neural tissue and cardiac muscle tissue during or after a myocardial infract (MI).

Simple surface methods for warming, whether treating accidental hypothermia or reversing hypothermia, include wrapping the patient in warming blankets or immersing the patient in a warm water bath. If the hypothermia is not too severe, and the need to reverse the hypothermia is not to urgent, these methods may be sufficient. However, normal thermoregulatory responses such as vasoconstriction of capillary beds at the surface of the body and arterio-venous shunting of blood away from the skin act to make the surface application of warmth very slow and inefficient.

Where hypothermia is desired, for example where a patient has suffered a stroke, an attempt may be made to cool the patient by application of cooling blankets or alcohol rubs. These attempts to induce hypothermia by application of surface cooling are slow and inefficient since the application of a cold blanket or cold alcohol to the patient's skin will triggers these thermoregulatory responses. Furthermore, surface cooling will be extremely uncomfortable for any awake patient. As an additional confounding factor, the patient is often induced to shiver, greatly increasing the amount of heat generated by the body, perhaps by a factor of five or more. This is and often sufficient to make further reduction of patient temperature impossible. Shivering also markedly increases the discomfort of the patient, sometimes to the degree that continued surface cooling is not possible.

Sometimes warmed or cooled breathing gases or warm infusions are applied to heat or cool a patient. These are also slow and poorly controlled since the amount of heat that can be added or removed is limited by the amount of infusate and the limitations on the temperature of the gas or infusate that can be used without harming the patient.

A very invasive method of controlling the temperature of a patient is sometimes employed in which the patient's blood is shunted through a cannula (attached to a vein such as the inferior vena cava) to an external pump, and then pumped back into the patient's body. The blood removed from the patient is heated or cooled externally before it is reintroduced into the patient's body. An example of such a by-pass arrangement is the Cardio-Pulmonary By-pass system (CPB) often used in open heart surgery. This by-pass method, once it is initiated, is both fast and effective in adding or removing heat from a patient's blood and in exercising control over the patient's body temperature in general, but has the disadvantage of involving a very invasive medical procedure which requires the use of complex equipment, a team of highly skilled operators, is generally only available in a surgical setting, and because of these complexities, is extremely expensive and requires a long time to initiate. In fact, it generally cannot begin until after the patient's thorax has been surgically opened, cannot re-warm after the thorax is closed. Furthermore, such a by-pass method also involves mechanical pumping of blood, which is generally very destructive to the blood resulting for example in hemolysis. For this last reason, use of by-pass for more than four hours is generally considered undesirable which limits the use of this technique for lengthy temperature control.

Another method for adding or removing heat that does not involve pumping the blood with an external, mechanical pump include a method of treating or inducing hypothermia or hyperthermia by means of a heat exchange catheter placed in the bloodstream of a patient was described in U.S. Pat. No. 5,486,208 to Ginsburg, the complete disclosure of which is incorporated herein by reference. The Ginsburg patent discloses a method of controlling the temperature of a body by adding or removing heat to the blood by inserting a heat exchange catheter having a heat exchange region into the vascular system and exchanging heat between the heat exchange region and the blood to affect the temperature of a patient. One method disclosed for doing so includes inserting a catheter having a heat exchange region comprising a balloon into the vasculature of a patient and circulating warm or cold heat exchange fluid through the balloon while the balloon is in contact with the blood.

In general, the transfer of heat between the heat exchange region of such a catheter and the flowing blood may be expressed by the following formula:

$$Q=US\Delta T$$

where Q is the heat transfer rate in watts, U is overall heat transfer coefficient, S is the surface area of the interface between the heat exchange region and the flowing blood, and $\Delta T$ is the temperature difference between the flowing blood and the heat exchange region. In order to maximize the speed and control of heat transfer between the heat exchange catheter described below and the blood of a patient, the heat transfer rate (Q) must be maximized.

However, for a given heat exchange catheter, for example the catheter described in the Detailed Description below, the surface area of contact between the heat exchange region and the blood (S) is fixed.

For heat exchange between the catheter and the blood, the $\Delta T$ is also limited. The blood is generally the same temperature of the body, between 37° C. and 32° C. The heat exchange region cannot be maintained much below 0° C. or it will freeze the blood in contact with the heat exchange region. Any temperature above about 50° C. is generally considered harmful to the blood, so the heat exchange region generally will not be maintained at a temperature significantly below 0° C. or above 50° C.

The variable U is determined by a number of different variables including the material of the heat exchange catheter, the material of the flowing fluid (blood) the rate of flow, and the like. For a given heat exchange catheter in the blood, the material of the catheter is fixed, and the heat exchange nature of the blood and the rate of blood flow are generally not within the control of the physician. With all these parameters fixed or limited, it would be extremely advantageous to devise a way to further enhance heat transfer where the above conditions exist. This invention makes possible such an enhancement.

SUMMARY OF THE INVENTION

The present invention provides a catheter system for controlling the body temperature of a patient by modifying the temperature of blood flowing within a blood vessel of the patient. The present system comprises a catheter body having a heat exchange region, the heat exchange region having a heat exchange surface in contact with the blood; and a source of motion connected, directly or indirectly, to the heat exchange region so as to impart motion to the heat exchange surface while the heat exchange surface is in contact with blood flowing thereover sufficient to induce gentle mixing of the blood as it flows over the heat exchange surface.

In accordance with the present invention, movement of the heat exchange surface (i.e.: the surface of the heat exchange region which is disposed in contact with the blood flowing thereover) enhances heat exchange between the catheter system and the blood flow. Specifically, such movement of the heat exchange surface disrupts smooth fluid flow over the heat exchange surface, thereby causing mixing of the blood, for example, stirring or eddies in the blood passing thereover, sufficient to enhance the heat exchange between the flowing blood and the heat exchange surface.

The present invention thus provides methods for treating or inducing hypothermia or hyperthermia by inserting the present catheter body (either with a catheter shaft attached to or having as an integral part, a moving heat exchange surface) into a blood vessel of the patient and selectively transferring heat either to or from the blood flowing through the vessel. It enhances the ability to exchange heat, thereby enhancing both the ability to induce or treat hypothermia or hyperthermia and the ability to rapidly and precisely control the body temperature of the patient.

In the various aspects of the invention in which a fluid filled heat exchange balloon is used, movement of the heat exchange surface of the balloon also beneficially disrupts fluid flow within the balloon, and specifically adjacent the interior of the heat exchange surface, thereby causing stirring or eddies in the heat exchange fluid passing therethrough, thereby enhancing the heat exchange between the heat exchange fluid and the heat exchange surface. In preferred aspects, the heat transfer balloon may be a multi-lobed, multi-lumen balloon. In accordance with the present invention, movement of the heat exchange surface is induced by a source of motion connected, directly or indirectly, to the heat exchange region. In various aspects of the invention, this source of motion comprises a wire extending longitudinally through at least a portion of the catheter body and a transducer adapted to move the wire, in some instances in the ultrasonic range.

Alternatively, systems are also provided to cause motion of the heat exchange surface by providing a source of motion comprises a wire extending longitudinally through at least a portion of the catheter body and mechanisms to rotate the wire, wherein at least a portion of the wire has a non-symmetric cross section or a radial protrusion extending therefrom. In addition, systems having bent wires, which when rotated cause a distal end of the catheter to move in a stirring motion are also provided. Alternatively, in the case of a fluid filled heat exchange balloon, the movement may be induced or supplemented in the heat exchange surface of the balloon by a source of motion which introduces movement into the fluid column of the heat exchange fluid passing therethrough.

Yet another source of motion may be provided by a fluid flow deflecting vane or like structure on the catheter body, on the heat exchange region, or on a guide wire passed through at least a portion of the catheter into the flowing bloodstream. The flowing blood deflects against the vane, causing motion of the heat exchange region.

Accordingly, the present invention provides a variety of different mechanisms which may optionally be used to cause movement of the heat exchange surface of the catheter body, which preferably causes gentle mixing motion of the blood passing over the heat exchange surface of the catheter. Such mixing (by causing stirring or eddy formation in the fluid flow) has the beneficial effect of increasing heat transfer between the heat exchange region of the catheter and the blood flowing over the catheter. Depending on the characteristics of the fluids, the heat exchange surface, and the temperatures involved, this may increase heat exchange by 25% or more compared to a non-moving heat exchange surface. Accordingly, the present invention provides systems to rapidly, efficiently and controllably exchanging heat with the blood of a patient so the temperature of the patient or target tissue within the patient can more effectively and rapidly be altered, or maintained at some target temperature.

The present invention further provides a method of controlling the body temperature of a patient by modifying the temperature of blood flowing within a blood vessel of the patient. These methods preferably comprise advancing a catheter body having a heat exchange surface into the patient's blood vessel such that the heat exchange surface is in contact with the patient's blood; causing the temperature of the heat exchange surface to be different from that of the blood such that heat transfer occurs between the heat exchange surface and the patient's blood; and moving the heat exchange surface of the heat exchange region, thereby disrupting the fluid flow over the heat exchange surface of the heat exchange region of the catheter body. In addition, such movement of the heat exchange surface may also disrupt fluid flow within the heat exchange region of the catheter itself, for example, along the interior of the heat exchange surface in the case of a fluid filled heat exchange catheter. Accordingly, in optional aspects, the movement is imparted directly to the fluid column of heat exchange fluid passing through the catheter.

In various aspects of this method, different techniques may be used to cause movement of the catheter body, including ultrasound application to a wire running along through at least a portion of the catheter body. Rotation of a wire extending longitudinally through the catheter body (with the wire having either a non-symmetric cross section, a bend, or a number of bends therein, or a radial protrusion extending therefrom) may also be used. When such a wire is rotated, it will cause the heat exchange surface of the heat exchange region to move.

As used herein, "movement" of the present heat exchange surface of the heat exchange region of the catheter body comprises moving at least a portion of the heat exchange surface such that at least a portion of the catheter body deflects in various radial directions relative to the flow of the blood in the vessel, (i.e.: directions perpendicular to the central longitudinal axis of the catheter in the blood vessel), with the catheter body also preferably moving in various radial directions, in either a serpentine or stirring motion.

In additional aspects, "movement" of the heat exchange surface may also encompass movement of a portion of the catheter body back and forth in an axial direction, i.e.: along the central longitudinal axis of the catheter body, or rotational motion, i.e. rotation of a non-smooth heat exchange surface around the central longitudinal axis of the catheter body, or any combination of these various motions.

In addition, in the case of a fluid filled heat exchange balloon, the movement of the heat exchange surface of the balloon may be induced or supplemented by a source of motion which introduces movement into the fluid column of the heat exchange fluid passing therethrough.

BRIEF DESCRIPTION OF THE DRAWINGS

FIG. 1 is an illustration of a catheter having a longitudinally extending wire passing therealong, with an ultrasound transducer mounted to move the wire in a radial direction.

FIG. 2 is an illustration of a catheter having a longitudinally extending wire passing therealong, with an ultrasound transducer mounted to move the wire in an axial direction.

FIG. 3 is an illustration of a catheter having a longitudinally extending wire passing therealong, the wire being bent at one location.

FIG. 4 is an illustration of a catheter having a longitudinally extending wire passing therealong, the wire having a protrusion extending radially therefrom.

FIG. 5 is a sectional end view of a catheter having a longitudinally extending wire passing therealong, the wire having a non-symmetrical cross section.

FIG. 6 illustrates a distal end view of the present catheter system, showing various radial directions.

FIG. 7 illustrates a catheter with a multilobed balloon heat exchange region attached to the distal end of the catheter body and with a guide wire therethrough having several bends on the guide wire.

FIG. 8 illustrates a catheter with flow deflecting vanes and having a guide wire therethrough having a flow deflecting vane on the distal end of said guide wire.

FIG. 9A illustrates a heat exchange catheter having a deflecting wire therein.

FIG. 9B illustrates a heat exchange catheter having a deflecting wire therein, said deflecting wire in the retracted position.

DESCRIPTION OF THE SPECIFIC EMBODIMENTS

Figure 10:
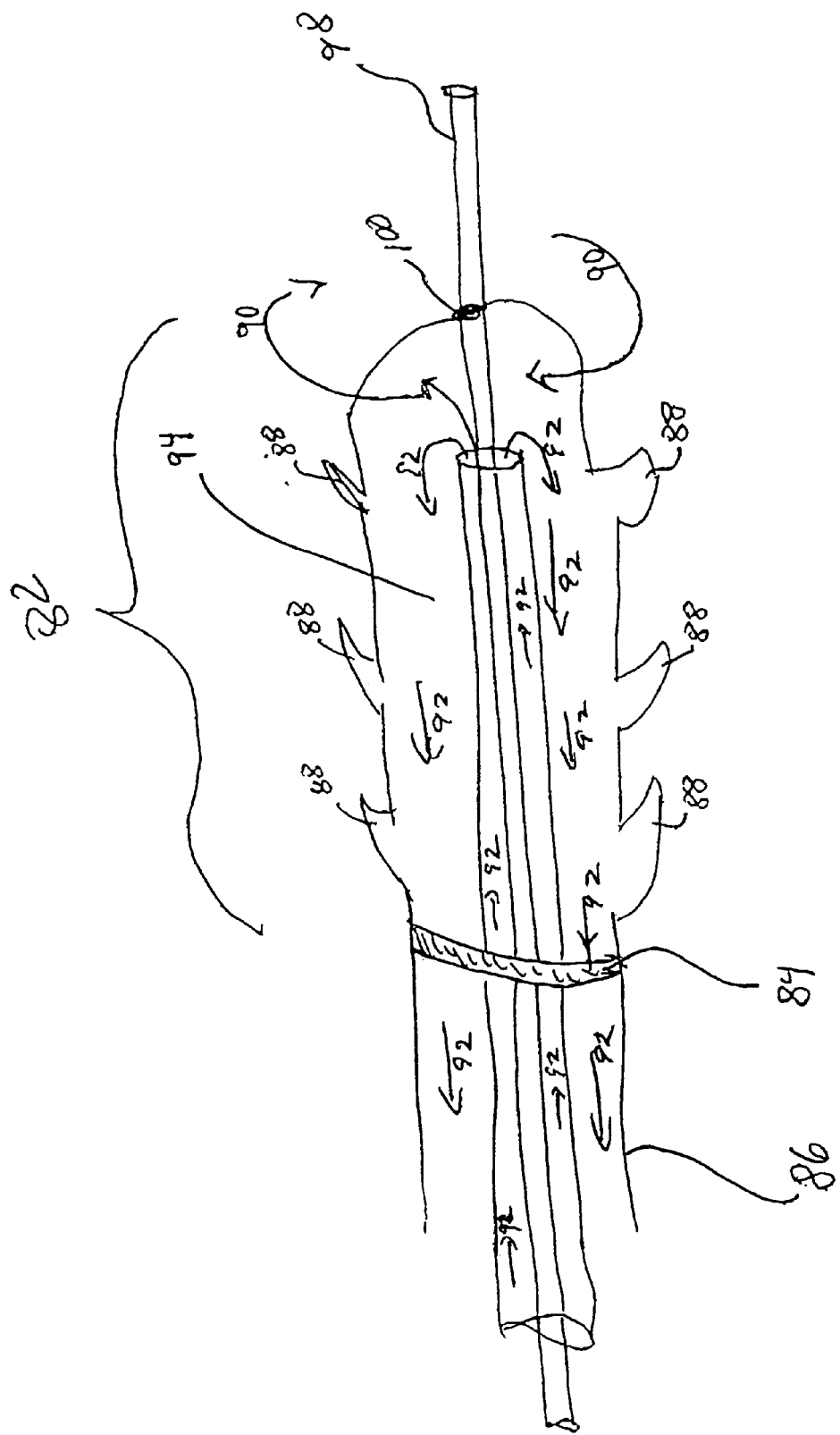
FIG. 10 shows a heat exchange catheter with a rotating heat exchange surface.

The present invention provides apparatus and methods for controlling the body temperature of a patient by modifying the temperature of blood flowing within a blood vessel of the patient. In preferred aspects, the present invention provides a catheter body having a heat exchange region disposed in contact with the blood, and a system for moving the heat exchange surface of the heat exchange region of the catheter body, thereby breaking up or disrupting fluid flow thereover, by stirring and by causing eddy formation in blood flowing over a heat exchange surface of the heat exchange region of the catheter body.

A variety of different catheter bodies and a variety of different sources of motion, including, but not limited to those described herein as examples, may be used to cause the heat exchange surface of the heat exchange region of the catheter body to move. In various aspects, the actual column of heat exchange fluid passing through a heat exchange balloon may also move, as will be explained.

Accordingly, by way of example, FIGS. 1 to 6 illustrate various approaches to causing a heat exchange surface of a catheter to "move", in accordance with the present invention.

Referring first to FIG. 1, a heat exchange catheter body 10 is provided. Catheter body 10 may comprise any type of heat exchange catheter. For example, catheter body 10 may comprise a fluid filled balloon heat exchange catheter (as illustrated in FIG. 6) or a heat exchange catheter having resistance heaters disposed therein (as illustrated in FIG. 1). Suitable examples of heat exchange catheter systems which may comprise the present catheter body 10 are also found in various U.S. patents.

It is to be understood that the present invention may be adapted for use with a wide variety of different temperature regulating catheter systems. For example, in accordance with the present invention, the catheter system used may comprise a catheter system adapted for warming the body fluid passing thereover (for example, a system having an electric heater disposed therein, or alternatively, a system pumping a heat exchange fluid therethrough). In addition, the catheter system used may comprise a catheter system adapted for cooling the body fluid passing thereover (for example, a system pumping a cooled fluid flow therethrough).

In the embodiment of the invention shown in FIG. 1, catheter body 10 comprises a heat exchange region 11 in which a resistance heater 13 is disposed. In this aspect, surface 12 comprises the heat exchange surface.

In accordance with the present invention, movement of a heat exchange surface is induced by a source of motion.

In various aspects of the invention, this source of motion comprises a wire extending longitudinally through at least a portion of the catheter body and a transducer adapted to move the wire. For example, catheter body 10 has a longitudinally extending wire 20 passing through at least a portion thereof, and a transducer 22 mounted therein.

In accordance with the present invention, the source of motion is connected to the heat exchange region so as to impart movement to the heat exchange surface. This may be accomplished by a number of different approaches, including, but not limited to the examples set out below.

Returning to FIG. 1, transducer 22 may be attached to wire 20 to cause wire 20 to move. Transducer 22 preferably comprises an ultrasound transducer, but need not be so.

In one preferred aspect, transducer 22 is preferably positioned in contact with wire 20 such that it moves the proximal end 21 of wire 20 back and forth in radial directions R1.

In this aspect of the invention, vibrational energy passes (as waves) along wire 20 from its proximal end 21 to its distal end 23 such that catheter 20 moves. In this aspect, the movement of wire 20 (and catheter 10) will be substantially in radial direction R1, causing the catheter to "wag" in a two dimensional plane (i.e.: in the plane of the page on which FIG. 1 is illustrated, see also direction R1 in FIG. 6 as explained below).

As such, movement of catheter body 10 by transducer 22 results in a movement being directly transmitted along at least a portion of the length of catheter body 10, thereby causing heat exchange surface 12 of heat exchange region 11 of catheter body 10 to move.

Alternatively, however, transducer 22 may instead be connected to proximal end 21 of wire 20 such that wire 20 "shakes" or "trembles", i.e. moving in 3 dimensions (e.g.: R1, R2 and R3 as illustrated in FIG. 6 as explained below), such that movement of wire 20 is not limited to movement within the plane of the page on which FIG. 1 is illustrated. Accordingly, it is to be understood that the system shown in FIG. 1 may be adapted for vibrational movement in either of these two or three dimensional modes, depending upon how transducer 22 is coupled with proximal end 21 of wire 20.

FIG. 6 illustrates an end view of the present catheter system (with catheter 10 and wire 20 straightened such that wire 20 is co-linear with a central longitudinal axis extending through catheter 10), showing various radial directions. Back and forth movement which only occurs in radial directions R1 constitutes (2 dimensional) movement in one preferred plane. In contrast, movement which occurs in all of radial directions R1, R2 and R3 (and in all radial directions at angles therebetween) constitutes three dimensional movement.

In the present invention, "movement" of the heat exchange surface may also be accomplished by repeatedly deflecting at least a portion of the catheter body in various radially outward directions (i.e.: directions perpendicular to the central longitudinal axis of the catheter). In accordance with the present invention, such radial deflection thus may thus result in a "serpentine" movement of the portion of the catheter body which comprises heat exchange surface 12. This is distinguished from a simple "pulsing" movement in which the central longitudinal axis of the catheter body would instead remain at the same position, for example, with a heat surface of a fluid filled heat exchange balloon simply moving radially inwards and outwards, with the balloon inflating (i.e.: with its heat exchange surface moving outwardly from the center of the catheter body) and deflating (i.e.: with its heat exchange surface moving inwardly toward the center of the catheter body).

In accordance with the present invention, however, the movement resulting from at least a portion of the catheter body repeatedly deflecting in various radially outward R1 directions comprises movement of the catheter body back and forth in two opposing radial directions (i.e.: with the catheter body "wagging" in a preferred plane). Alternatively, however, such movement may result in at least a portion of the catheter body repeatedly deflecting in more than two opposing R1, R2 and R3 radial directions with at least a portion of catheter body 10 either: (1) "shaking" or "trembling" such that a central axis of the catheter body moves in various random radial directions over time or, (2) a portion of catheter body 10 rotates around the central longitudinal axis extending through a remaining portion of the catheter.

In the "shaking" or "trembling" aspect, the central axis of the catheter body (which is shown in FIG. 6 as being co-linear with wire 20) will preferably tend to return to a central position over time.

Returning to FIG. 1, the frequency of movement of heat exchange surface 11 of catheter body 10 may be in an ultrasonic range, but need not be so. For example, movement at a frequency below the ultrasonic range is also contemplated. In this lower frequency aspect of the invention, the present catheter body may simply move gently at an easily visible frequency, for example one or two cycles per second. The amplitude (i.e. the radial distance in direction R to which the "moving" heat exchange region moves) may be greater at lower frequencies, but in any event, it will be constrained by the width of the blood vessel in which the heat exchange region is located. Therefore, some axial motion may as well may be induced in order to disrupt the layered flow of blood over the heat exchange region.

Modification to this design is also possible. For example, transducer 22 may instead be coupled to distal end 23 of wire 20, with vibratory motion moving from distal end 23 to proximal end 21 of the wire.

Referring next to FIG. 2, heat exchange catheter body 10 is again provided. Catheter body 10 has a longitudinally extending wire 20 passing therealong, and a transducer 22A mounted therein. In this aspect, transducer 22A is positioned in contact with wire 20 such that it moves the proximal end of wire 20 back and forth in axial direction A. In this aspect of the invention, distal end 23 of wire 20 is preferably attached to the distal end of the catheter. In this aspect of the invention, vibrational energy passes along wire 20 from its proximal end 21 to its distal end 23 (with portions of wire 20 alternatingly being in tension and compression) such that catheter 20 moves. In this aspect, the movement of catheter 20 will be substantially in axial direction A.

Referring next to FIG. 3, the source of motion may also comprise a wire extending longitudinally through at least a portion of the catheter body with a mechanism adapted to rotate the wire. In one aspect, a distal portion of the catheter body rotates around a central longitudinal axis A1 extending generally through catheter body 10, as follows.

Heat exchange catheter body 10 is provided. Catheter body 10 has a longitudinally extending wire 20 passing therethrough. Wire 20 is slightly bent at kink or bend 25 (the angle of which is exaggerated in FIG. 3 for clarity of illustration). Proximal end 21 of wire 20 is attached to rotation system 30 (which preferably comprises a motor). Rotation system 30 rotates wire 20 about axis A1—A1 such that the distal end 15 of catheter 10 (and distal end 23 of wire 20) rotate about axis A1—A1, with distal end 15 moving in a "stirring" motion, being disposed at roughly the same radial distance form axis A1—A1. As such, various portions along length 17 of catheter body 10 will preferably remain at the same distances from the central longitudinal axis A1—A1 of the catheter as wire 20 is rotated.

Axis A1—A1 preferably is co-linear with the central longitudinal axis of the catheter when the catheter is fully straightened out. As can be seen in FIG. 3, a large (proximal) portion of the catheter may remain co-linear with axis A1—A1, such that catheter body movement is instead generally limited to movement in a distal region of the catheter (comprising the heat exchange region).

In various optional aspects, wire 20 may have more than one bend therealong. Together, these multiple bends may position distal end 15 of catheter 10 such that it is not co-axial with axis A1—A1. For example, in another aspect as shown in FIG. 7, wire 20 may have a plurality of bends therealong which taken together position distal end 15 of catheter body 10 co-axial with axis A1—A1. In this aspect of the invention, distal end 15 of catheter body 10 will remain disposed on axis A1—A1 while wire 20 is rotated. However, body portions 10A and 10B would preferably extend in opposing radial directions R1. When wire 20 is rotated, relative movement of body portions 10A and 10B would tend to disrupt fluid flow passing over catheter 10.

In alternate aspects, movement may be caused by a non-symmetrical cross section (or radial protrusion) disposed at a distal end of the wire such that, as the wire is rotated, the distal end of the catheter will circle around a central longitudinal axis extending through the majority of the length of the catheter body (with the distal end of the catheter tending to remain at the same distance from this central longitudinal axis), as follows.

Referring next to FIG. 4, heat exchange catheter body 10 is provided. Catheter body 10 has a longitudinally extending wire 20 passing therethrough. Wire 20 has a protrusion 27 extending radially therefrom. Proximal end 21 of wire 20 is attached to rotation system 30 (which preferably comprises a motor). Rotation system 30 rotates wire 20 about axis A1—A1 such that protrusion 27 also rotates about axis A1—A1 such that distal end 15 of catheter body 10 (and distal end 23 of wire 20) is caused to rotate about axis A1—A1, causing at least the distal portion of catheter body 10 to move.

Referring next to FIG. 5, heat exchange catheter body 10 is provided. Catheter body 10 has a longitudinally extending wire 20A passing therethrough. Wire 20 has at least a portion of which has a non-symmetrical cross section. Wire 20 is rotated about axis A1—A1 (for example, by a rotation system identical or similar to rotation system 30 of FIGS. 3 and 4). Since wire 20A is non-symmetrical in cross section, rotation of wire 20A will cause catheter body 10 to move. Wire 20A may optionally have a non-symmetrical cross section along its entire length, or only along a small portion of its length. When the nonsymmetrical portion of wire 20A is disposed near its distal end 23, rotation of wire 20A causes the distal end of catheter body 10 to rotate about axis A1—A1, causing heat exchange surface 12 catheter body 10 to move.

Referring again to FIG. 7, in which the heat exchange region comprises a fluid filled balloon, such a balloon may be a simple single lumen balloon, or may comprise a multi-lumen, multi-lobbed balloon. The catheter body in this instance comprises a shaft portion 51 and a multi-lobed balloon 55 attached to the distal end of the catheter shaft. The heat exchange region may also be formed integral with the shaft, as was the case in the embodiments previously discussed. In these systems, the heat exchange surface of the heat exchange region comprises the surface of a heat exchange balloon. In such systems, heat exchange occurs between both the heat exchange fluid and the balloon surface, and also between the balloon surface and the blood flowing thereover. When using a multi-lumen, multi-lobbed balloon, the various lobes of the balloon may preferably wrapped or braided around a central lumen, as shown.

In a supplemental aspect of the invention, where the catheter exchanges heat with the blood by means of circulating a heat exchange fluid through the heat exchange region of the catheter, movement may also be imparted to the heat exchange region by introducing a movement into the fluid column circulating through the heat exchange region. This may be done, for example, by attaching an ultrasound movement generator to the hub of the catheter to impart the movement to the fluid column.

Such movement of a fluid column of heat exchange fluid is distinguished from existing systems which simply pulse fluid through a heat exchange balloon, i.e. inflating and deflating a balloon to the degree necessary to prevent blood clot formation. In contrast, the present system can induce movement in the fluid column without simply expanding and contracting the outer balloon diameter to the degree of the prior art.

Where heat exchange is occurring between two flowing fluids, it is most efficient to have counter-current flow. That is, the flow of the heat exchange liquid is counter to the flow direction of the fluid with which it is exchanging heat. Since a heat exchange catheter might be inserted into blood vessels in various ways which would result in the natural blood flowing being different in different instances (i.e. proximal to distal, or distal to proximal), the present catheter may optionally be advantageously constructed such that the direction of the fluid flow in the portion of the heat exchange region exposed to the flow of the body fluid could be adjusted to flow in either direction to permit the catheter could be inserted into the blood vessel in either direction, with the direction of the flow of the heat exchange fluid adjusted to flow counter to the flow in the vessel.

In another aspect of the invention, as illustrated in FIG. 8, the source of motion is a flow deflecting vane that is deployed in the flowing bloodstream within the vessel. The flow deflecting vane may be on the catheter shaft 50 or may be located directly on the heat exchange region of the catheter 52. Alternatively, it may be located on a guide wire, for example on the distal end of a guide wire 54, that is passed through at least a portion of the catheter body and out into the bloodstream. The flow deflecting vane, wherever located in the flowing blood, moves about in the bloodstream and thereby imparts motion to the heat exchange region.

Although the illustration shows flow deflecting vanes on all three locations, it will be understood by those of skill in the art that a single flow deflecting vane, or several flow deflecting vanes on a single structure, or any combination may be utilized and the catheter system will still be within the contemplation of this invention. Likewise, the flow deflecting vane may be a rigid structure protruding from a portion of the catheter or from the guide wire, or may be the structural contour of the heat exchange region, shaft, or guide wire designed to introduce motion when deployed in a flowing bloodstream. For example, if the surface of a multi-lobed heat exchange balloon has asymmetrical protrusions that induce motion, this is within the contemplation of this invention. Likewise, although a guide wire was used in this illustration, a similar wire structure such as a temperature probe extending from the catheter might be configured to induce motion and that too would be within the contemplation of this invention.

Another system for imparting motion to the heat exchange surface comprises a pull wire and a source of variable tension on the pull wire for alternatively pulling and releasing the wire. Such a system is shown in FIGS. 9A and 9B. A catheter having a heat exchange surface 70 has a pull wire 72 extending therethrough to an attachment location 74 near the heat exchange region of the catheter. A source of tension, for example a source of reciprocal motion 76 is attached to the pull wire. The attachment location is asymmetrical, for example on one side of a circular lumen, so that when the wire is pulled, the heat exchange surface is curved in a radial direction, and when the wire is pushed or relaxed, the heat exchange surface is relatively straight along the catheter axis. By repeatedly pulling and then relaxing the pull wire, the heat exchange surface is moved within the flowing bloodstream so as to enhance heat exchange.

Rotational motion of the heat exchange surface, where the surface has features that may act to stir the flowing fluid, will also enhance heat exchange. For example, in FIG. 10, a catheter has an inflow lumen 80 and a coaxial heat exchange region 82. A fluid tight bearing 84 is located between the proximal catheter body 86 and the heat exchange region. The surface of the heat exchange region is formed with a series of protrusions 88 such as flow deflecting vanes. In this case, the blood flow over the surface would impart rotational motion as indicated by arrows 90 of the heat exchange region, which would rotate relative to the catheter shaft 86. The bearing 84 would permit the rotation while maintaining the fluid tight seal so that heat exchange fluid indicated by the arrows 92 could flow down the inflow lumen 80, into the interior lumen of the heat exchange region 94 and back down the outflow lumen 96. A working lumen 98 could also be present in such a catheter, with the working lumen located down the center of the inflow lumen 80. The working lumen may extend distal of the heat exchange region. If so, a bearing may exist where the working lumen exits the heat exchange region 100. Alternatively, that location may be a point of attachment, so that rotation of the working lumen serves to rotate the heat exchange region. A source of rotation motion attached to the proximal end of the working lumen, for example outside the patient, could thus serve to impart rotational motion to the heat exchange surface.

The heat exchange catheters of this invention may also comprise a temperature sensor 106 disposed within the catheter body.

The embodiments set forth herein are merely exemplary of systems operating in accordance with the present invention. Such exemplary embodiments are not limiting. Rather, it is to be understood that the present invention encompasses all systems set forth in accordance with the attached claims, and those modifications which would be apparent to one skilled in the art.

What is claimed is:

1. A catheter system for controlling body temperature of a patient by modifying the temperature of blood flowing within a blood vessel of the patient, the system comprising:
   a catheter body having a heat exchange region, the heat exchange region having a heat exchange surface that comes in contact with the patient's blood;
   an apparatus for cooling the heat exchange region such that heat will be exchanged across the heat exchange surface, thereby cooling the patient's blood;
   a source of motion which imparts movement to the heat exchange surface while heat is being exchanged between the heat exchange surface and the patient's blood to cool the patient's blood;
   wherein the source of motion comprises: a wire extending longitudinally through a portion of the catheter body; and a transducer connected to the wire, the transducer adapted to move the wire in an axial direction.

2. The system of claim 1 wherein the catheter body comprises a catheter shaft and a heat exchange region, said heat exchange region attached to the distal end of said shaft.

3. The system of claim 1 wherein the heat exchange region is integral with said catheter shaft.

4. The system of claim 1 where the source of motion is connected indirectly to the heat exchange region.

5. The system of claim 1 wherein the source of motion is directly attached to the catheter body so as to impart motion to the heat exchange region.

6. The system of claim 1 wherein the source of motion is a flow deflecting vane attached to the catheter body and placed in a flowing stream of fluid.

7. The system of claim 1, wherein the heat exchange surface comprises: an outer surface of a fluid filled heat exchange balloon.

8. The system of claim 1, wherein the transducer comprises an ultrasound transducer.

9. The system of claim 1, wherein the transducer is attached to a proximal end of the wire.

10. The system of claim 1, wherein the heat exchange surface comprises a plurality of heat-transfer fins extending from the catheter body.

11. The system of claim 1, wherein the heat exchange surface comprises an internal heating system disposed within the catheter body.

12. The system of claim 11, wherein the internal heating system comprises a resistance heater.

13. The system of claim 1, further comprising a pumping system for passing heat exchange fluid through the catheter body, the heat exchange fluid being at a different temperature than the blood flowing in the blood vessel.

* * * * *